(12) United States Patent
Hwang et al.

(10) Patent No.: US 10,023,596 B2
(45) Date of Patent: Jul. 17, 2018

(54) METHOD FOR PREPARING RACEMIC OR OPTICALLY ACTIVE D- OR L-A-GLYCEROPHOSPHORYL CHOLINE SOLIDS

(71) Applicant: ENZYTECH. LTD., Daejeon (KR)

(72) Inventors: Soon Ook Hwang, Daejeon (KR); Dae Myoung Yun, Daejeon (KR); Chang-min Kim, Daejeon (KR)

(73) Assignee: ENZYTECH, LTD., Daejeon (KR)

( * ) Notice: Subject to any disclaimer, the term of this patent is extended or adjusted under 35 U.S.C. 154(b) by 0 days.

(21) Appl. No.: 15/468,136

(22) Filed: Mar. 24, 2017

(65) Prior Publication Data

US 2017/0190724 A1    Jul. 6, 2017

Related U.S. Application Data

(63) Continuation of application No. PCT/KR2015/010086, filed on Sep. 24, 2015.

(30) Foreign Application Priority Data

Sep. 26, 2014 (KR) .................. 10-2014-0129581

(51) Int. Cl.
C07F 9/113    (2006.01)
C07B 55/00    (2006.01)

(52) U.S. Cl.
CPC .............. *C07F 9/113* (2013.01); *C07B 55/00* (2013.01)

(58) Field of Classification Search
CPC .................................. C07F 9/113; C07B 55/00
See application file for complete search history.

(56) References Cited

U.S. PATENT DOCUMENTS 5,523,450 A    6/1996  Evans et al.
9,617,288 B2 *  4/2017  Hwang .............. C07F 9/65515

FOREIGN PATENT DOCUMENTS

| KR | 10-0262281 B | 7/2000 |
| KR | 10-2007-0119176 A | 12/2007 |
| WO | 2012/124907 A | 9/2012 |

\* cited by examiner

*Primary Examiner* — Golam M M Shameem
(74) *Attorney, Agent, or Firm* — LRK Patent Law Firm

(57) ABSTRACT

The present invention is characterized in that racemic or optically active D- or L-α-glycerophosphoryl choline solids are prepared from liquid type racemic or optically active D- or L-α-glycerophosphoryl choline using an organic solvent. The present invention can produce solids at a high yield more easily through phase transformation rather than a method using a difference in solubility in a solvent, which is an existing method.

9 Claims, 10 Drawing Sheets

METHOD FOR PREPARING RACEMIC OR OPTICALLY ACTIVE D- OR L-A-GLYCEROPHOSPHORYL CHOLINE SOLIDS

CROSS-REFERENCES TO RELATED APPLICATIONS

This Application claims the benefit of priority and is a Continuation application of the prior International Patent Application No. PCT/KR2015/010086, with an international filing date of Sep. 24, 2015, which designated the United States, and is related to the Korean Patent Application No. 10-2014-0129581, filed Sep. 26, 2014, the entire disclosures of all applications are expressly incorporated by reference in their entirety herein.

BACKGROUND OF THE INVENTION

1. Field of the Invention

The present invention relates to a method of preparing a solid form of racemic or optically active D or L-α-glycerophosphorylcholine, and more particularly, to a method of preparing a solid form of racemic or optically active D or L-α-glycerophosphorylcholine from a conventional liquid phase of racemic or optically active D or L-α-glycerophosphorylcholine through phase change using an organic solvent.

2. Description of Related Art

Racemic or optically active D or L-α-glycerophosphorylcholine is a compound represented by Formula 1 below, and is known to have excellent effects in treatment of senile cognitive impairment (decreased memory, confusion, loss of sense of direction, decreased motivation and spontaneity, decreased concentration) such as secondary symptoms due to cerebrovascular deficiency and degenerative organic brain syndromes and senile pseudo-depression such as emotional and behavioral changes (anxiety disorder, irritability, lack of interest), and specifically, is known to be an excellent drug that normalizes functions of damaged neurons and abnormalities of the cholinergic system due to acetylcholine deficiency by promoting production of acetylcholine, a neurotransmitter in the brain.

Formula 1

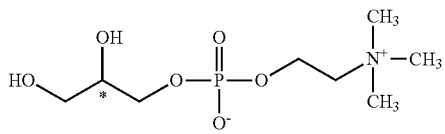

wherein * indicates a chiral center and Formula 1 represents a racemic and optically active D or L-α-optical isomer.

Known methods of crystallizing liquid-phase α-glycerophosphorylcholine are as follows. First of all, in *J. Am. Chem. Soc.* 70, 1394-1399 (1948), it was reported that a water-containing glycerophosphorylcholine prepared by a pure synthetic method can be solidified in an alcohol solution, but no specific crystallization method or crystal structure was mentioned.

According to a method disclosed in Korean Patent No. 262,281, glycerophosphorylcholine is prepared by performing deacylation reaction by alcoholysis in a reactor containing basic ion exchange resins, lipophilic impurities are removed using non-polar adsorptive resins, the glycerophosphorylcholine is dissolved in methanol, to which an about 20-fold amount of n-butanol is further added, and then the mixture is subjected to vacuum concentration, followed by cooling and filtering to recover anhydrous crystals. However, in this method, it was reported that microcrystals having high hygroscopicity were formed, and there was no mention of specific crystal structure.

According to methods disclosed in Korean Patent Application Publications No. 10-2013-0063520 and No. 10-2013-0063521, conventional liquid-phase L-α-glycerophosphorylcholine is concentrated, dissolved in an alcohol solution, and seed crystals are added to trigger crystallization, followed by aging and filtering to obtain crystals of L-α-glycerophosphorylcholine in anhydrous form and L-α-glycerophosphorylcholine-type in the form of a monohydrate. However, the above methods have problems in that the methods use seed crystals and that yield is low due to crystal formation by difference in solubility.

According to a method disclosed in Korean Patent Application Publication No. 10-2001-7005577, L-carnitine, which is a hygroscopic solid, is polished with acetone and filtered to obtain solid L-carnitine. Until now, there has been no method of preparing solid glycerophosphorylcholine by such a method.

Accordingly, the present inventors have made intensive efforts to solve the problems of the conventional technologies, and as a result, have developed a method to solidify racemic or optically active D or L-α-glycerophosphorylcholine in a simpler and easier way and confirmed that the solidified D or L-α-glycerophosphorylcholine may be mass-produced at high purity and low cost, and thus the present invention was completed.

BRIEF SUMMARY OF THE INVENTION

The object of the present invention is to provide a method of mass-producing a solid form of racemic or optically active D or L-α-glycerophosphorylcholine in a simple manufacturing process and at low cost.

One aspect of the present invention provides a method of preparing a solid form of racemic or optically active D or L-α-glycerophosphorylcholine, wherein a liquid phase of racemic or optically active D or L-α-glycerophosphorylcholine represented by Formula 1 below undergoes phase change by adding one or more organic solvents selected from the group consisting of alcohols, hydrocarbons, ketones, ethers and cyanides and stirring the mixture.

Formula 1

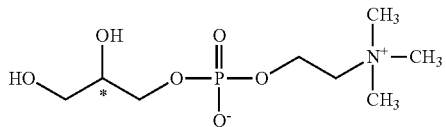

wherein * indicates a chiral center, and Formula 1 represents an isomer of racemic and optically active D or L-α-glycerophosphorylcholine.

Another aspect of the present invention provides solid powders of glycerophosphorylcholine, which are prepared according to the above method, wherein the solid powders exhibit peaks at 2θ diffraction angles of 11.9±0.2°, 14.2±0.2°, 19.8±0.2°, 25.3±0.2° and 40.4±0.2° in powder X-ray diffraction (XRD) analysis, and exhibit endothermic peaks in a range of 71±2° C. to 129±2° C. for endothermic onset temperature and endothermic peaks in a range of 100±2° C. to 137±2° C. for endothermic temperature in differential scanning calorimetry (DSC).

DETAILED DESCRIPTION OF THE INVENTION

Figure 1:
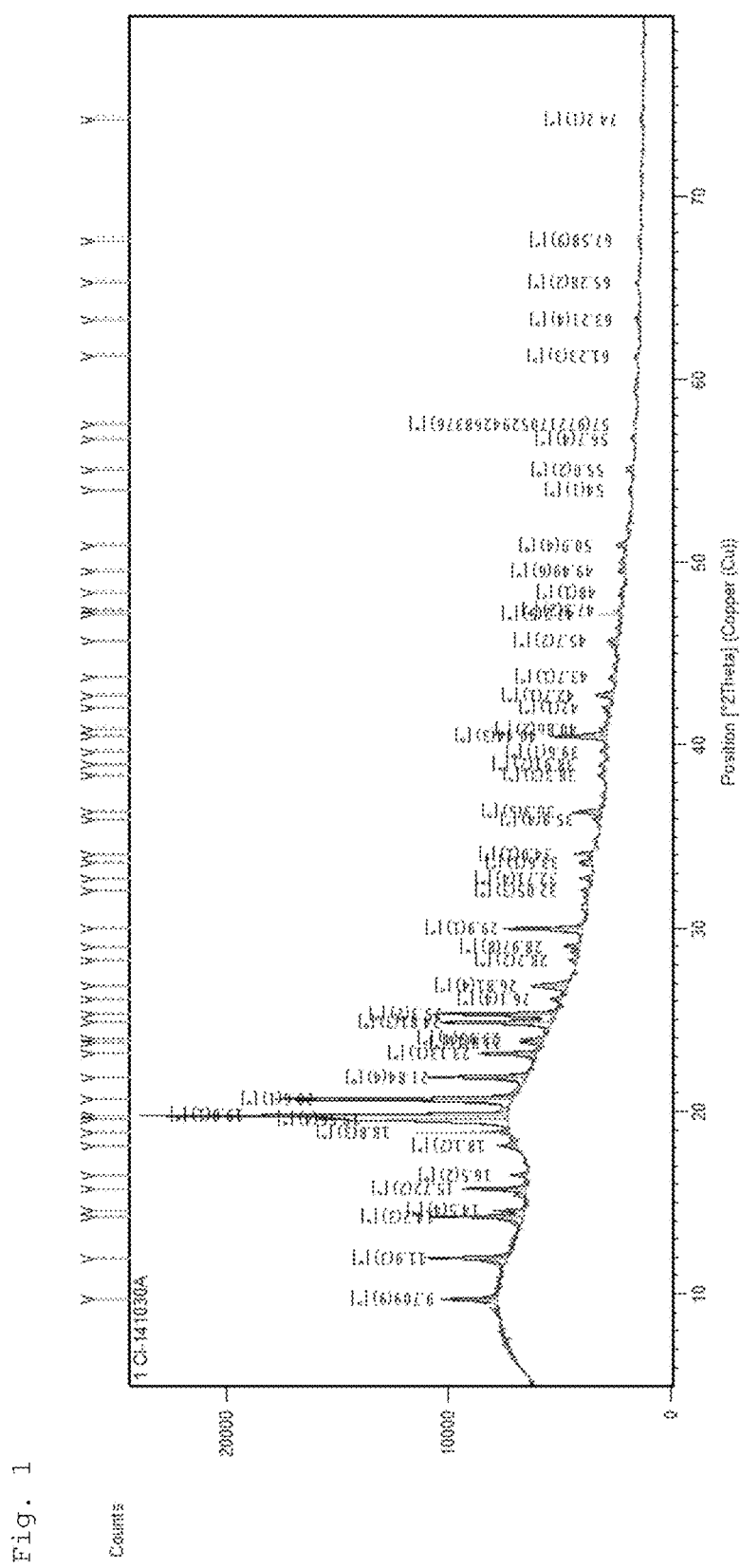
FIG. 1 is a result of powder X-ray diffraction (XRD) analysis of solid glycerophosphorylcholine prepared using hexane according to an embodiment of the present invention.

Unless otherwise defined, all terms (including technical and scientific terms) used herein have the same meaning as commonly understood by one of ordinary skill in the art. In general, nomenclature used herein and experimental methods described below are well known and commonly used in the art.

Unlike conventional methods using difference in solubility in a solvent, the present invention aimed to develop a method of preparing a solid form of racemic or optically active D or L-α-glycerophosphorylcholine from a liquid phase of racemic or optically active D or L-α-glycerophosphorylcholine through phase change using an organic solvent. In addition, the present invention was intended to demonstrate that this method was capable of preparing the solid form in an easier way and at a high yield.

Therefore, according to one aspect of the present invention, the present invention relates to a method of preparing a solid form of racemic or optically active D or L-α-glycerophosphorylcholine, wherein a liquid phase of racemic or optically active D or L-α-glycerophosphorylcholine represented by Formula 1 below undergoes phase change by adding one or more organic solvents selected from the group consisting of alcohols, hydrocarbons, ketones, ethers and cyanides and stirring the mixture. Further, another feature of the present invention is that powder X-ray diffraction (XRD), differential scanning calorimetry (DSC), and solid form may be different depending on solvents, stirring time or temperature. This can be confirmed from FIGS. 1 to 8.

Formula 1

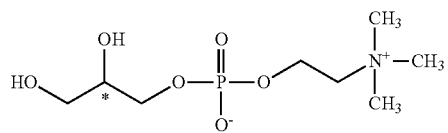

wherein * indicates a chiral center.

The present invention relates to a method of preparing a solid form of racemic or optically active D or L-α-glycerophosphorylcholine represented by Formula 1 below. According to the method, the solid form of racemic or optically active D or L-α-glycerophosphorylcholine is prepared by drying a liquid phase of racemic or optically active D or L-α-glycerophosphorylcholine to a moisture content of 0 to 10% by weight, and then adding the organic solvents in an amount of 1 to 20 times the volume of the liquid phase of racemic or optically active D or L-α-glycerophosphorylcholine and stirring at a temperature of 0 to 70° C. for 1 to 24 hours.

Formula 1

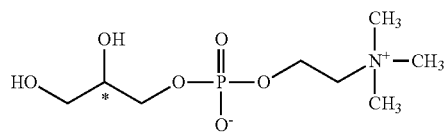

wherein * indicates a chiral center, and Formula 1 represents an isomer of optically active D or L-α-glycerophosphorylcholine.

In the present invention, the temperature is 0 to 70° C., preferably 30 to 60° C., and the stirring time is 0 to 24 hours, preferably 0.1 to 12 hours. When the stirring temperature is less than 0° C. or greater than 70° C., the production rate of solid decreases and overall yield may decrease.

In the present invention, the moisture content is 0 to 10% by weight, preferably 0 to 7% by weight. When the moisture content exceeds 10% by weight, the production rate of solid decreases and overall yield may decrease.

In the present invention, solvents selected from the group consisting of alcohols, hydrocarbons, ketones, ethers and cyanides may be used alone or in combination of two or more as the organic solvents. More preferably, solvents selected from the group consisting of alcohols having 1 to 8 carbon atoms, alkane having 1 to 8 carbon atoms, ketones having 1 to 8 carbon atoms, and ethers and cyanides having 1 to 8 carbon atoms may be used alone or in combination of two or more as the organic solvents.

For specific example, solvents selected from the group consisting of alcohol-based solvents such as methanol, ethanol, n-propanol, isopropanol, n-butanol, isobutanol, 2-methoxyethanol, 2-ethoxyethanol, 2-butoxyethanol, 1-phentanol, 2-phentanol, 3-phentanol, 1-hexanol, 2-hexanol, 3-hexanol, 1-heptanol, 2-heptanol, 3-heptanol, 1-octanol, 2-octanol, 3-octanol, ethylene glycol, and propylene glycol; hydrocarbon-based solvents such as dichloromethane, dichloroethane, n-pentane, n-hexane, cyclohexane, n-heptane, n-octane, toluene, xylene, naphtha, and petroleum benzin; halogenated hydrocarbon-based solvents such as chloroform, carbon tetrachloride, trichloroethylene, and perfluoropropane; ketone-based solvents such as acetone, methylethylketone, methylisobutylketone, and acetophenone; ether-based solvents such as propyl ether, n-butyl ether, tetrahydrofuran, diethyl ether, and t-butyl methyl ether; and cyanide solvents such as acetonitrile and the like may be used alone or in combination of two or more as the organic solvents, without being limited thereto.

In the present invention, the amount of the organic solvent to be used is 1 to 20 times, preferably 2 to 7 times. When the amount of the organic solvent is less than 1 time, the production rate of solid may decrease. On the other hand, when the amount is more than 20 times, cost may greatly increase.

In another aspect, the present invention relates to solid powders of glycerophosphorylcholine, which are prepared according to the above method, wherein the solid powders exhibit peaks at 2θ diffraction angles of 11.9±0.2°, 14.2±0.2°, 19.8±0.2°, 25.3±0.2° and 40.4±0.2° in powder X-ray diffraction (XRD) analysis, and exhibit endothermic peaks in a range of 71±2° C. to 129±2° C. for endothermic onset temperature and endothermic peaks in a range of 100±2° C. to 137±2° C. for endothermic temperature in differential scanning calorimetry (DSC).

The solid powders of glycerophosphorylcholine may exhibit peaks at 2θ diffraction angles of 11.9±0.2°, 14.2±0.2°, 19.8±0.2°, 25.3±0.2° and 40.4±0.2° in powder X-ray diffraction (XRD) analysis, and may exhibit an endothermic peak at 71±2° C. for endothermic onset temperature and at 100±2° C. for endothermic temperature, respectively, in differential scanning calorimetry (DSC);

the solid powders may exhibit peaks at 2θ diffraction angles of 9.7±0.2°, 11.9±0.2°, 14.2±0.2°, 19.8±0.2°, 25.3±0.2° and 40.4±0.2° in powder X-ray diffraction (XRD) analysis, and may exhibit an endothermic peak at 129±2° C. for endothermic onset temperature and at 137±2° C. for endothermic temperature, respectively, in differential scanning calorimetry (DSC);

the solid powders may exhibit peaks at 2θ diffraction angles of 11.9±0.2°, 14.2±0.2°, 19.8±0.2°, 25.3±0.2°, 29.9±0.2° and 40.4±0.2° in powder X-ray diffraction (XRD) analysis, and may exhibit an endothermic peak at 118±2° C. for endothermic onset temperature and at 132±2° C. for endothermic temperature, respectively, in differential scanning calorimetry (DSC); or the solid powders may exhibit peaks at 2θ diffraction angles of 11.9±0.2°, 14.2±0.2°, 15.7±0.2°, 19.8±0.2°, 25.3±0.2° and 40.4±0.2° in powder X-ray diffraction (XRD) analysis, may exhibit an endothermic peak at 105±2° C. for endothermic onset temperature and at 130±2° C. for endothermic temperature, respectively, in differential scanning calorimetry (DSC).

Hereinafter, the present invention is described in more detail with reference to examples. It will be apparent to those skilled in the art that these examples are for illustrative purposes only and that the scope of the present invention is not construed as being limited by these examples.

EXAMPLES

Example 1: Preparation of Solid Form of Optically Active L-α-glycerophosphorylcholine Using Isopropanol 10 g of a liquid phase of L-α-glycerophosphorylcholine having a moisture content of 10% was dried at a temperature of 105° C. for 3 hours to reduce the moisture content to about 6%. 100 ml of isopropanol was added thereto, and the mixture was stirred at a temperature of 50° C. for 5 hours.

Precipitated solid was filtered and dried to obtain 7.8 g (yield: 92%) of L-α-glycerophosphorylcholine as a white solid.

Example 2: Preparation of Solid Form of Optically Active L-α-glycerophosphorylcholine Using Heptane 10 g of a liquid phase of L-α-glycerophosphorylcholine having a moisture content of 16% was dried at a temperature of 105° C. for 4 hours to reduce the moisture content to about 5%. 50 ml of heptane was added thereto, and the mixture was stirred at a temperature of 60° C. for 6 hours.

Precipitated solid was filtered and dried to obtain 7.65 g (yield: 90%) of L-α-glycerophosphorylcholine as a white solid.

Example 3: Preparation of Solid Form of Optically Active L-α-glycerophosphorylcholine Using Hexane 20 g of a liquid phase of L-α-glycerophosphorylcholine having a moisture content of 14.5% was dried at a temperature of 105° C. for 5 hours to reduce the moisture content to about 3.5%. 60 ml of hexane was added thereto, and the mixture was stirred at a temperature of 50° C. for 30 minutes.

Precipitated solid was filtered and dried to obtain 15.73 g (yield: 92%) of L-α-glycerophosphorylcholine as a white solid.

Powder X-Ray Diffraction (XRD) Analysis

Powder X-ray diffraction (XRD) analysis of the solid prepared in Example 3 showed that the solid exhibited specific peaks at 2θ diffraction angles of 11.9±0.2°, 14.2±0.2°, 19.8±0.2°, 25.3±0.2° and 40.4±0.2° (FIG. 1).

Differential Scanning Calorimetry (DSC) Analysis

Figure 5:
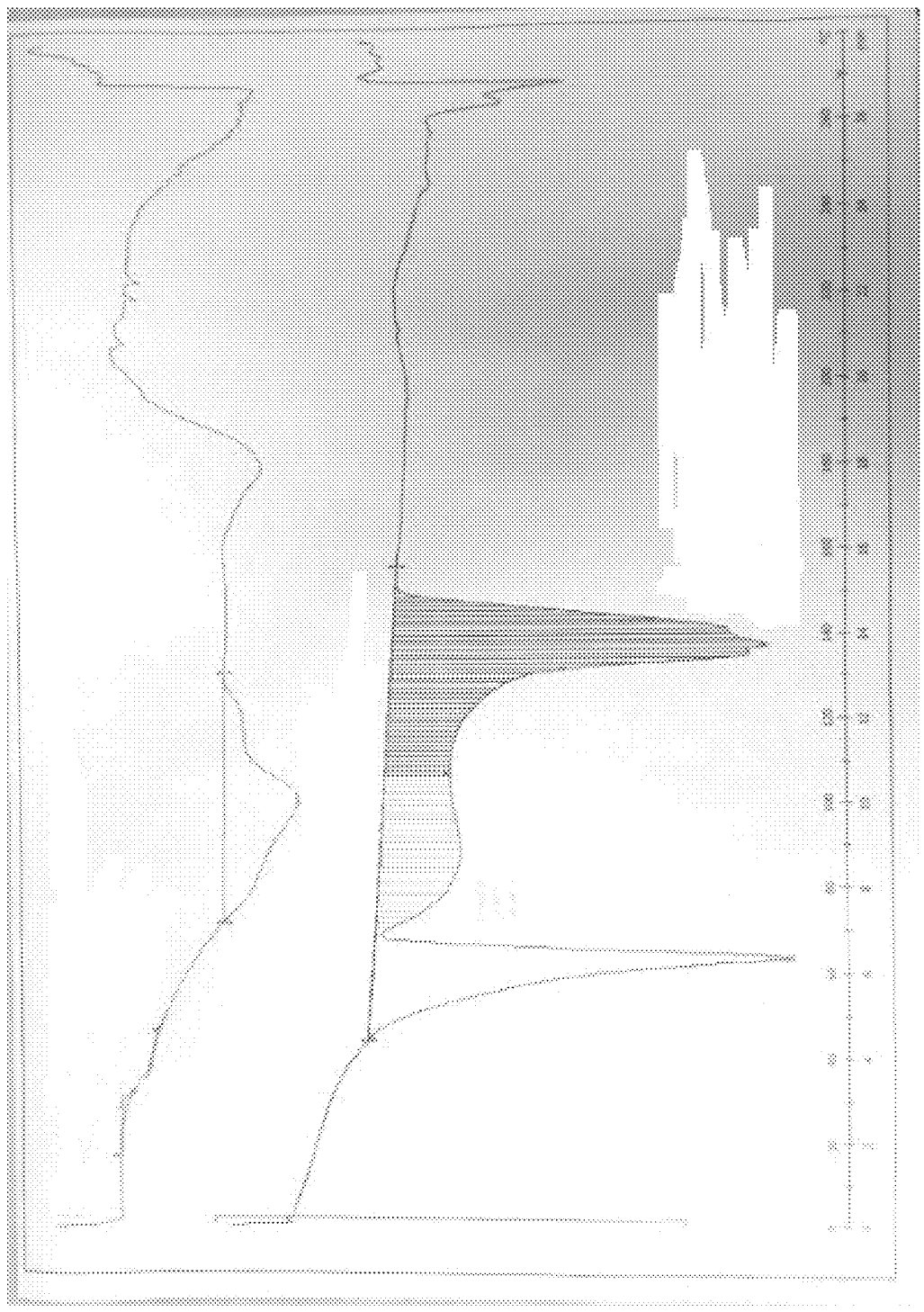
FIG. 5 is a result of differential scanning calorimetry (DSC) analysis of solid glycerophosphorylcholine prepared using hexane according to an embodiment of the present invention.

Differential scanning calorimetry (DSC) analysis of the solid prepared in Example 3 showed that the solid exhibited an endothermic peak at 71±2° C. for endothermic onset temperature and at 100±2° C. for endothermic temperature, respectively (Top curve in FIG. 5).

Example 4: Preparation of Solid Form of Optically Active L-α-glycerophosphorylcholine Using Hexane 20 g of a liquid phase of L-α-glycerophosphorylcholine having a moisture content of 14.5% was dried at a temperature of 105° C. for 5 hours to reduce the moisture content to about 3.5%. 60 ml of hexane was added thereto, and the mixture was stirred at a temperature of 40° C. for 6 hours.

Precipitated solid was filtered and dried to obtain 16.07 g (yield: 94%) of L-α-glycerophosphorylcholine as a white solid.

Powder X-Ray Diffraction (XRD) Analysis

Figure 2:
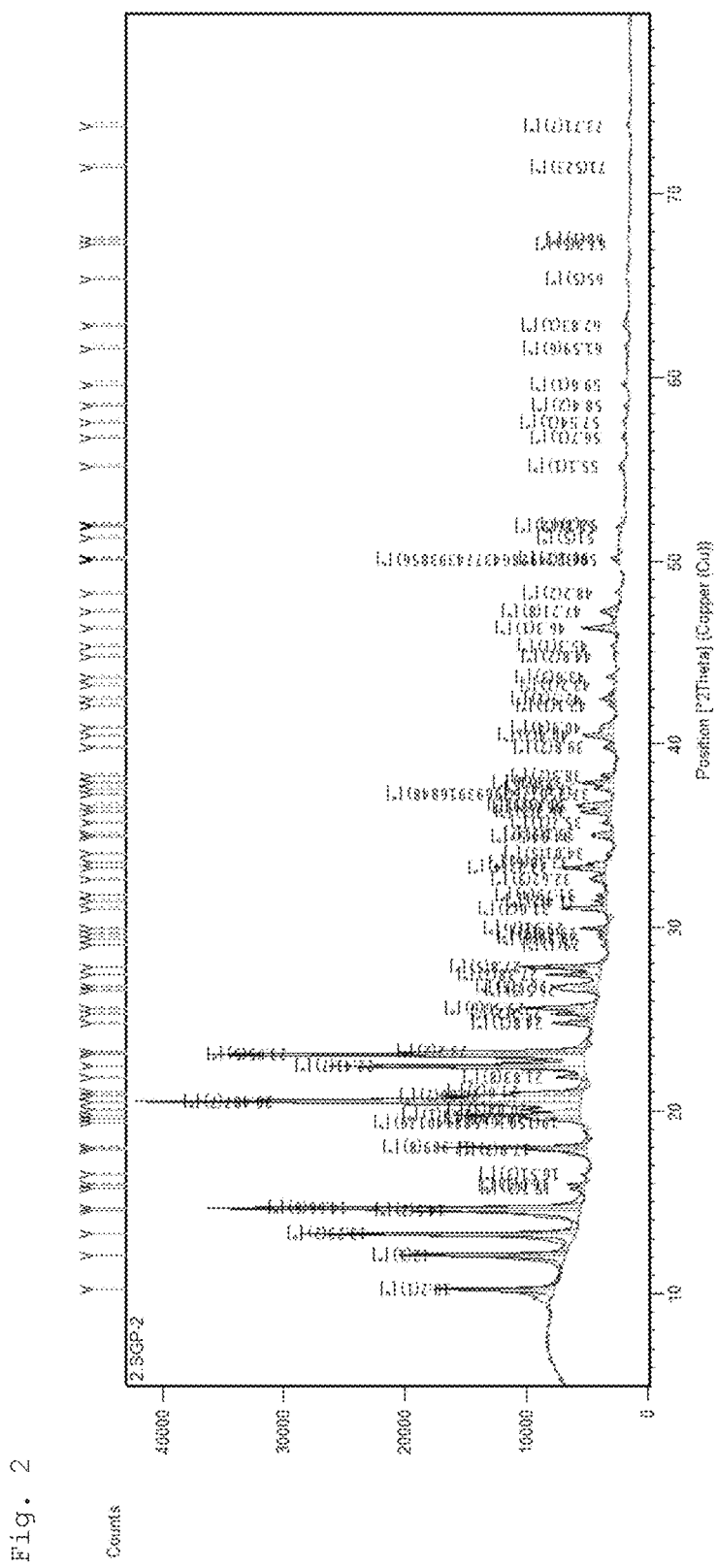
FIG. 2 is a result of powder X-ray diffraction (XRD) analysis of solid glycerophosphorylcholine prepared using hexane according to an embodiment of the present invention.

Powder X-ray diffraction (XRD) analysis of the solid prepared in Example 4 showed that the solid exhibited specific peaks at 2θ diffraction angles of 9.7±0.2°, 11.9±0.2°, 14.2±0.2°, 19.8±0.2°, 25.3±0.2° and 40.4±0.2° (FIG. 2).

Differential Scanning Calorimetry (DSC) Analysis

Differential scanning calorimetry (DSC) analysis of the solid prepared in Example 4 showed that the solid exhibited an endothermic peak at 129±2° C. for endothermic onset temperature and at 137±2° C. for endothermic temperature, respectively (Lower curve in FIG. 5).

Example 5: Preparation of Solid Form of Optically Active L-α-Glycerophosphorylcholine Using Octanol The moisture content of 4.5 g of a liquid phase of L-α-glycerophosphorylcholine was reduced to about 2% using MgSO$_4$. 45 ml of octanol was added thereto, and the mixture was stirred at a temperature of 50° C. for 4 hours.

Precipitated solid was filtered and dried to obtain 3.47 g (yield: 91%) of L-α-glycerophosphorylcholine as a white solid.

Example 6: Preparation of Solid Form of Optically Active L-α-glycerophosphorylcholine Using Isopropanol and Ethanol 20 g of a liquid phase of L-α-glycerophosphorylcholine having a moisture content of 15% was dried at a temperature of 105° C. for 4 hours to reduce the moisture content to about 5%. 5 ml of ethanol and 50 ml of isopropanol were added thereto, and the mixture was stirred at a temperature of 50° C. for 5 hours.

Precipitated solid was filtered and dried to obtain 15.81 g (yield: 93%) of L-α-glycerophosphorylcholine as a white solid.

Example 7: Preparation of Solid Form of Optically Active L-α-glycerophosphorylcholine Using Isopropanol and Methanol 10 g of a liquid phase of L-α-glycerophosphorylcholine was dried at a temperature of 105° C. for 4 hours to reduce a moisture content to about 6%. 5 ml of methanol and 50 ml of isopropanol were added thereto, and the mixture was stirred at a temperature of 50° C. for 4 hours.

Precipitated solid was filtered and dried to obtain 7.65 g (yield: 90%) of L-α-glycerophosphorylcholine as a white solid.

Example 8: Preparation of Solid Form of Optically Active L-α-glycerophosphorylcholine Using Acetone 10 g of a liquid phase of L-α-glycerophosphorylcholine having a moisture content of 15% was dried at a temperature of 105° C. for 5 hours to reduce the moisture content to about 3%. 100 ml of acetone was added thereto, and the mixture was stirred at a temperature of 50° C. for 4 hours.

Precipitated solid was filtered and dried to obtain 7.65 g (yield: 90%) of L-α-glycerophosphorylcholine as a white solid.

Example 9: Preparation of Solid Form of Optically Active L-α-glycerophosphorylcholine Using Acetone The moisture content of 15.6 g of a liquid phase of L-α-glycerophosphorylcholine was reduced to about 2% using MgSO$_4$. 156 ml of acetone was added thereto, and the mixture was stirred at a temperature of 0° C. for 20 hours.

Precipitated solid was filtered and dried to obtain 12.07 g (yield: 91%) of L-α-glycerophosphorylcholine as a white solid.

Example 10: Preparation of Solid Form of Optically Active L-α-glycerophosphorylcholine Using Methanol and Acetone 10 g of a liquid phase of L-α-glycerophosphorylcholine having a moisture content of 15% was dried at a temperature of 105° C. for 4 hours to reduce the moisture content to about 4%. 33 ml of methanol and 16 ml of acetone were added thereto, and the mixture was stirred at a temperature of 50° C. for 2 hours.

Figure 3:
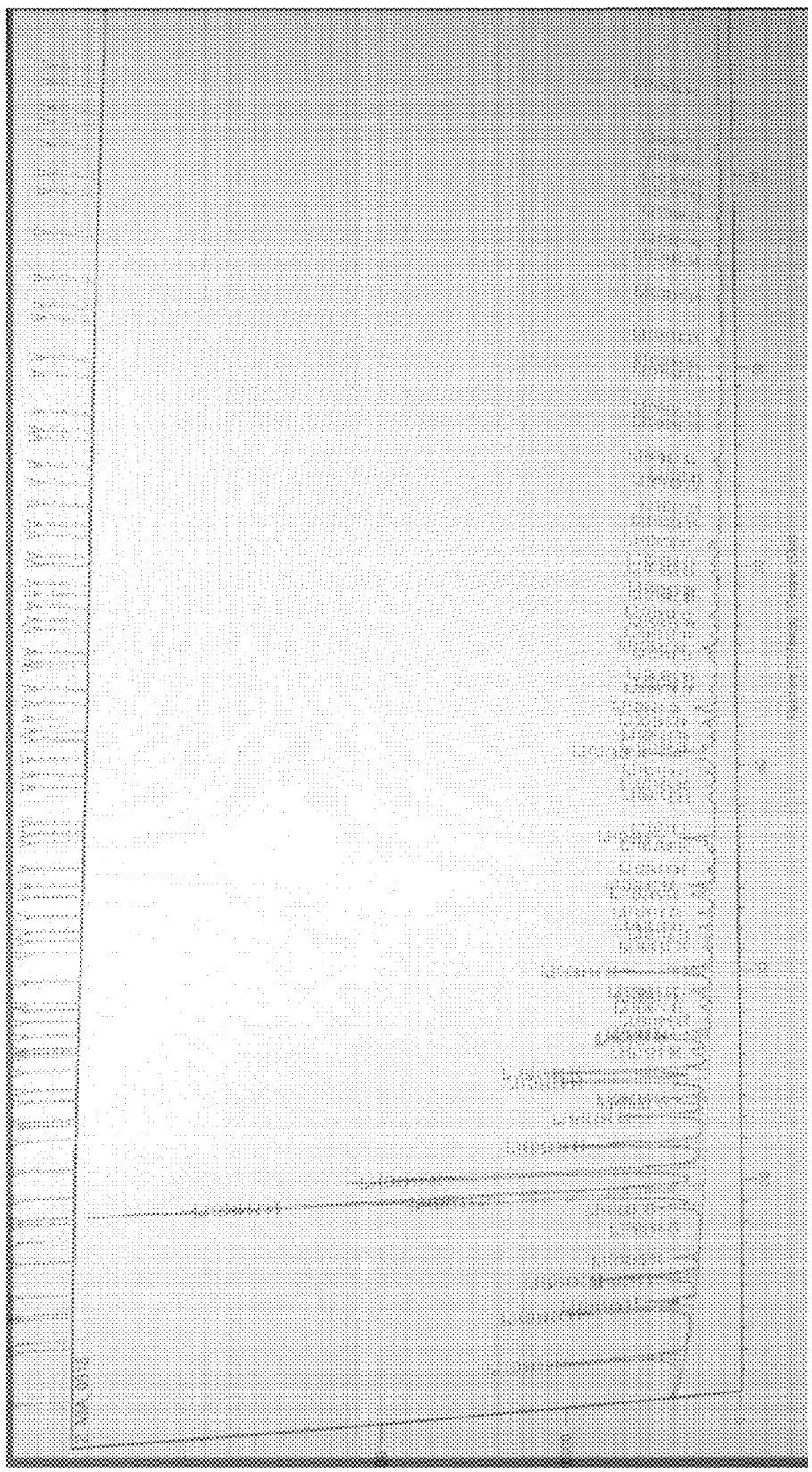
FIG. 3 is a result of powder X-ray diffraction (XRD) analysis of solid glycerophosphorylcholine prepared using methanol and acetone according to an embodiment of the present invention.

Precipitated solid was filtered and dried to obtain 7.99 g (yield: 94%) of L-α-glycerophosphorylcholine as a white solid Powder X-Ray Diffraction (XRD) Analysis Powder X-ray diffraction (XRD) analysis of the solid prepared in Example 10 showed that the solid exhibited specific peaks at 2θ diffraction angles of 11.9±0.2°, 14.2±0.2°, 19.8±0.2°, 25.3±0.2°, 29.9±0.2° and 40.4±0.2° (FIG. 3).

Differential Scanning Calorimetry (DSC) Analysis

Figure 6:
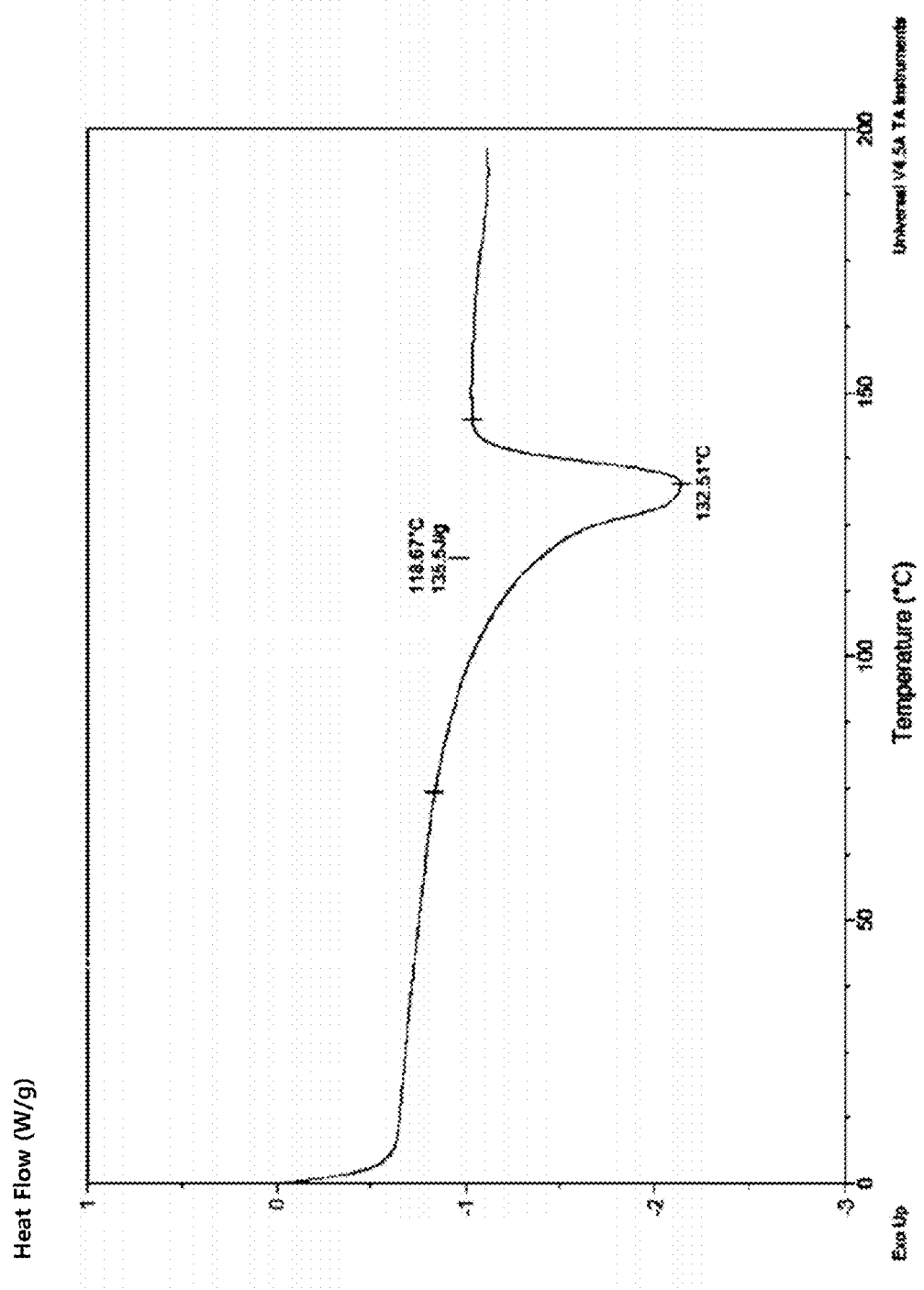
FIG. 6 is a result of differential scanning calorimetry (DSC) analysis of solid glycerophosphorylcholine prepared using methanol and acetone according to an embodiment of the present invention.

Differential scanning calorimetry (DSC) analysis of the solid prepared in Example 10 showed that the solid exhibited an endothermic peak at 118±2° C. for endothermic onset temperature and at 132±2° C. for endothermic temperature, respectively (FIG. 6).

Microscope Analysis

Figure 9:
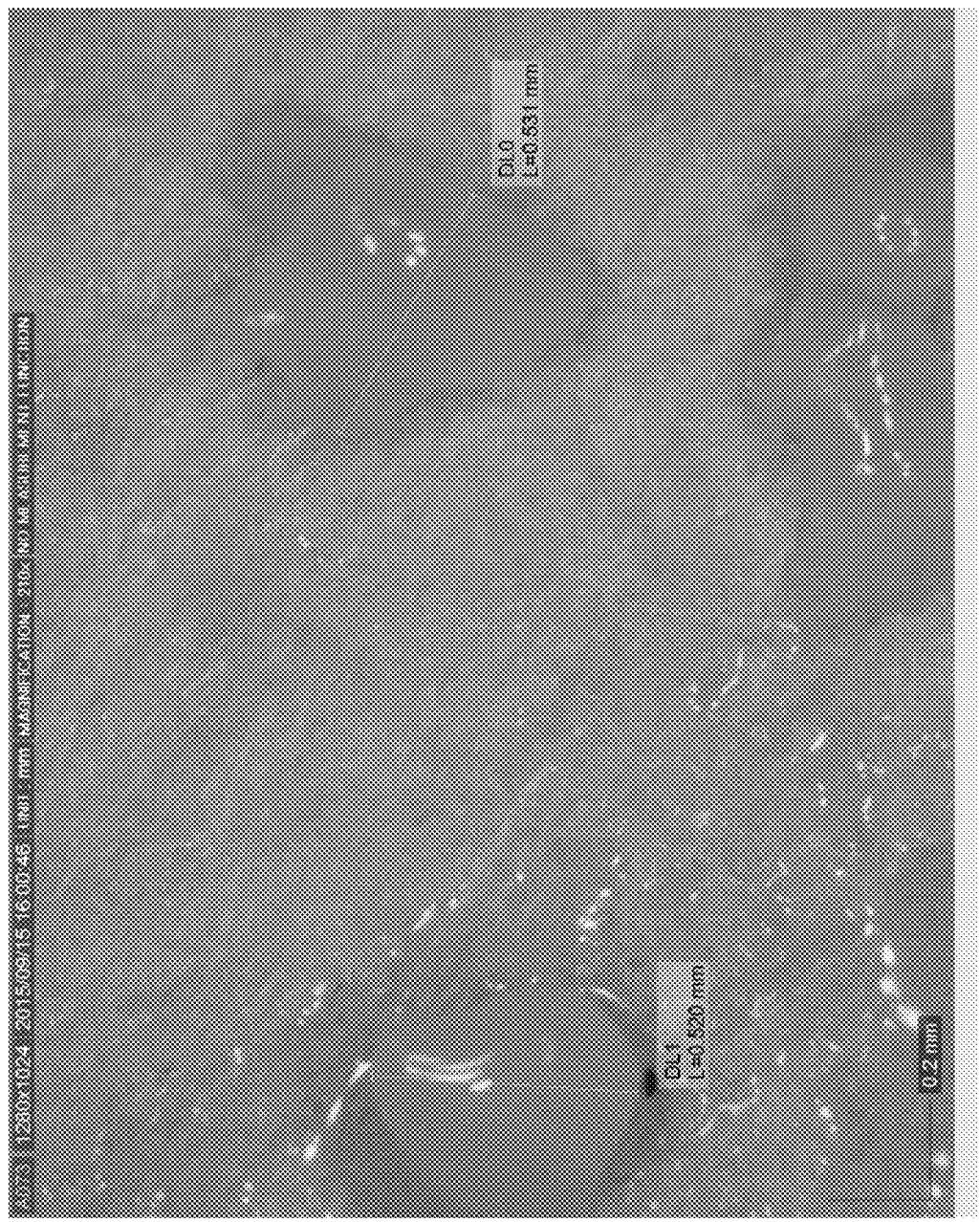
FIG. 9 is a microscopic analysis result of solid glycerophosphorylcholine prepared using isopropanol according to an embodiment of the present invention.

The solid prepared in Example 10 was analyzed by a microscope and the analysis result is shown in FIG. 9.

Example 11: Preparation of Solid Form of Optically Active L-α-glycerophosphorylcholine Using Isopropanol and Acetonitrile 10 g of a liquid phase of L-α-glycerophosphorylcholine having a moisture content of 15% was dried at a temperature of 105° C. for 4 hours to reduce the moisture content to about 4%. 10 ml of isopropanol and 50 ml of acetonitrile were added thereto, and the mixture was stirred at a temperature of 50° C. for 5 hours.

Precipitated solid was filtered and dried to obtain 8.08 g (yield: 95%) of L-α-glycerophosphorylcholine as a white solid.

Powder X-Ray Diffraction (XRD) Analysis

Figure 4:
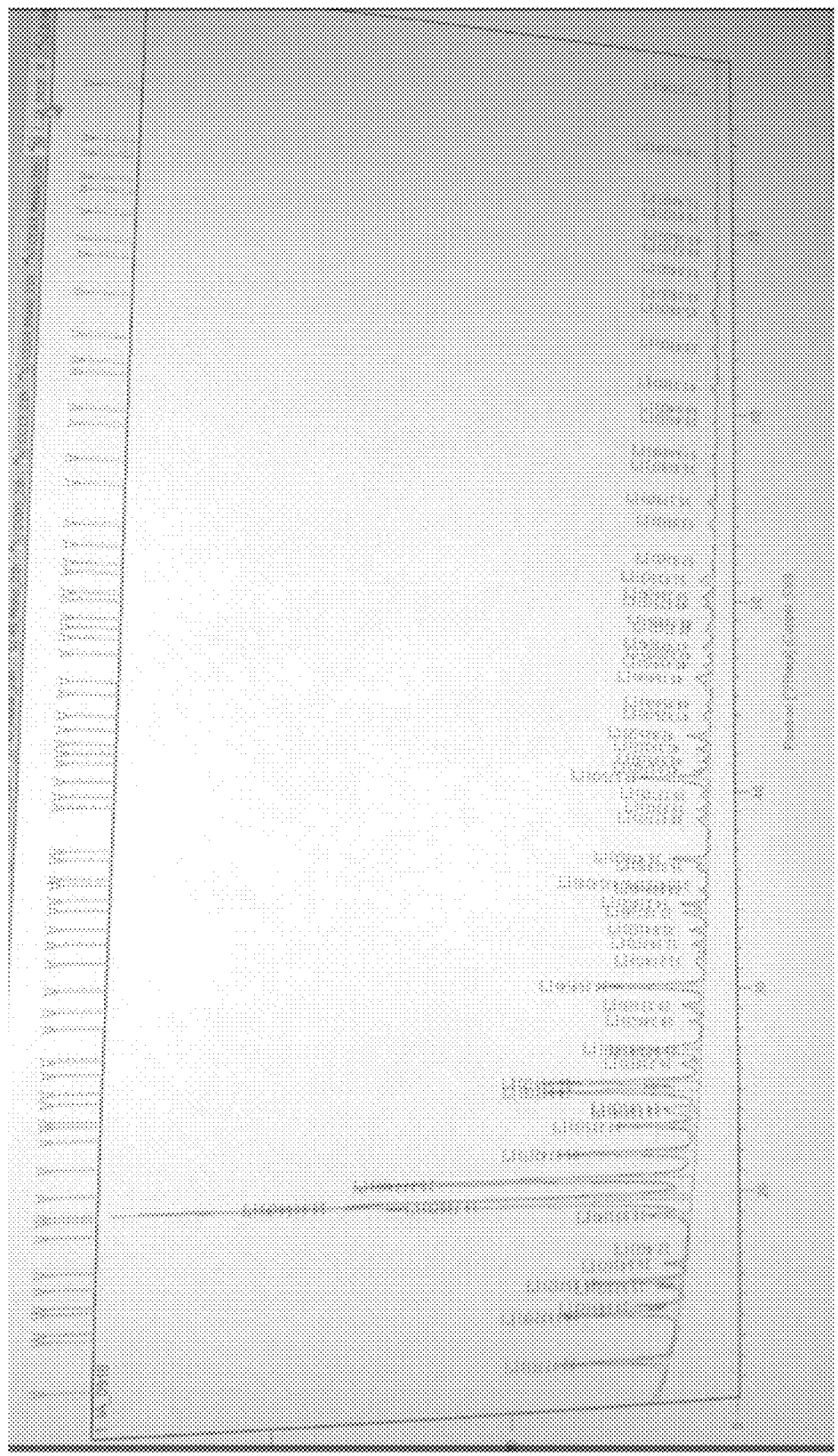
FIG. 4 is a result of powder X-ray diffraction (XRD) analysis of solid glycerophosphorylcholine prepared using isopropanol and acetonitrile according to an embodiment of the present invention.

Powder X-ray diffraction (XRD) analysis of the solid prepared in Example 11 showed that the solid exhibited specific peaks at 2θ diffraction angles of 11.9±0.2°, 14.2±0.2°, 5.7±0.2°, 19.8±0.2°, 25.3±0.2° and 40.4±0.2° (FIG. 4).

Differential Scanning Calorimetry (DSC) Analysis

Figure 7:
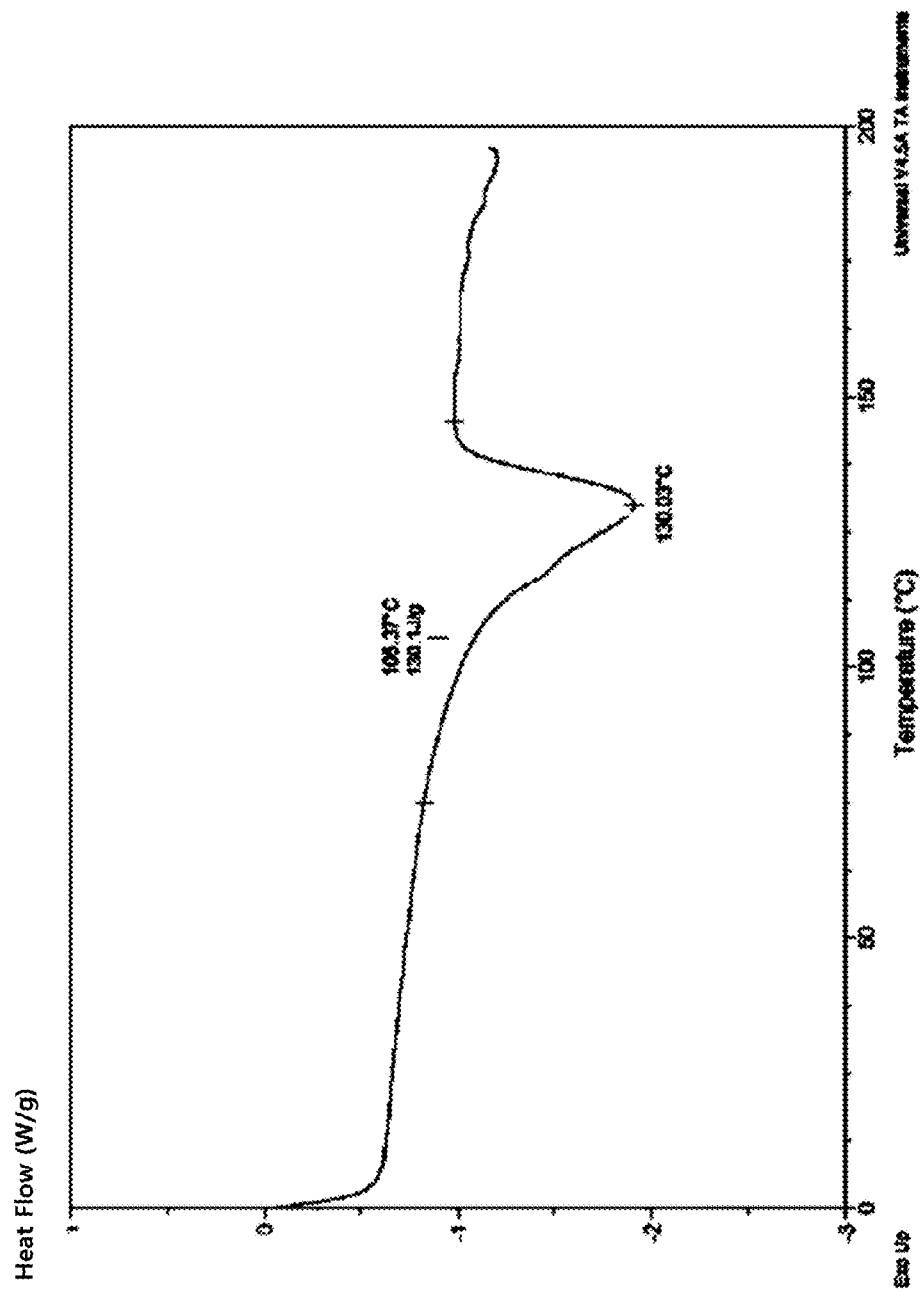
FIG. 7 is a result of differential scanning calorimetry (DSC) analysis of solid glycerophosphorylcholine prepared using isopropanol and acetonitrile according to an embodiment of the present invention.

Differential scanning calorimetry (DSC) analysis of the solid prepared in Example 11 showed that the solid exhibited an endothermic peak at 105±2° C. for endothermic onset temperature and at 130±2° C. for endothermic temperature, respectively (FIG. 7).

Microscope Analysis

Figure 10:
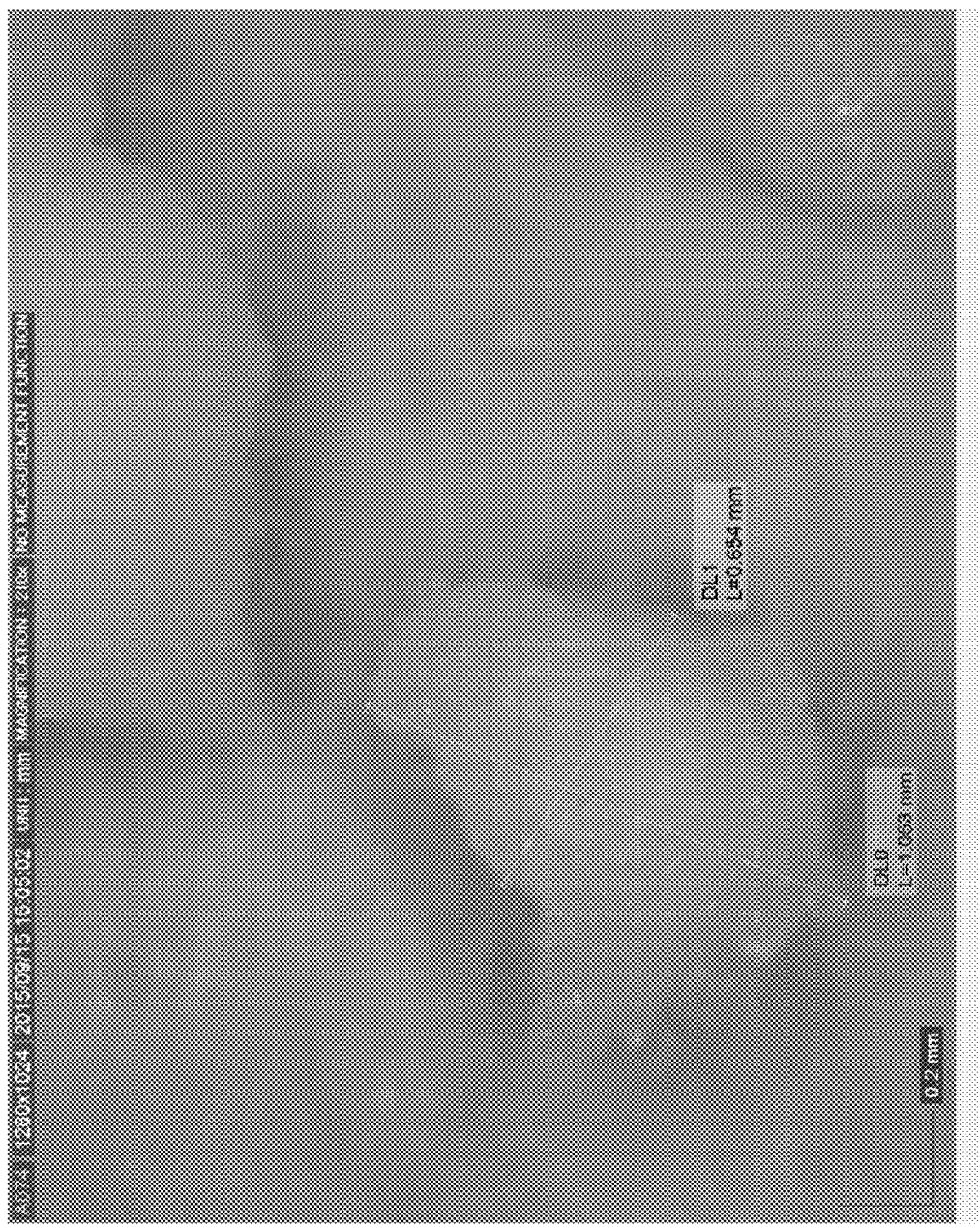
FIG. 10 is a microscopic analysis result of solid glycerophosphorylcholine prepared using hexane according to an embodiment of the present invention.

The solid prepared in Example 11 was analyzed by a microscope and the analysis result is shown in FIG. 10.

Example 12: Preparation of Solid Form of Optically Active L-α-glycerophosphorylcholine Using Isopropanol and Acetonitrile 10 g of a liquid phase of L-α-glycerophosphorylcholine having a moisture content of 15% was dried at a temperature of 105° C. for 4 hours to reduce the moisture content to about 4%. 10 ml of isopropanol and 30 ml of acetonitrile were added thereto, and the mixture was stirred at a temperature of 30° C. for 5 hours.

Precipitated solid was filtered and dried to obtain 7.82 g (yield: 92%) of L-α-glycerophosphorylcholine as a white solid.

Example 13: Preparation of Solid Form of Optically Active L-α-Glycerophosphorylcholine Using t-Butyl Methyl Ether 10 g of a liquid phase of L-α-glycerophosphorylcholine having a moisture content of 15% was dried at a temperature of 105° C. for 4 hours to reduce the moisture content to about 4%. 50 ml of t-butyl methyl ether was added thereto, and the mixture was stirred at a temperature of 50° C. for 40 minutes.

Precipitated solid was filtered and dried to obtain 8.08 g (yield: 95%) of L-α-glycerophosphorylcholine as a white solid.

Comparative Example 1

Preparation of Crystals of Optically Active L-α-glycerophosphorylcholine Using Ethanol Reference was made to the method disclosed in Korean Patent Application Publication No. 10-2013-0063520.

23 ml of ethanol was added to 11.5 g of powders of L-α-glycerophosphorylcholine and the powders were sufficiently dissolved at 50° C. The solution containing L-α-glycerophosphorylcholine was cooled to 9° C. and stirred for 5 hours. However, crystals were not formed. That is, no solid was produced when seed crystals were not administered as in Korean Patent Application Publication No. 10-2013-0063520.

In the case of the method of Comparative Example 1 (Korean Patent Application Publication No. 10-2013-0063520), L-α-glycerophosphorylcholine is sufficiently dissolved in alcohol at a high temperature, and then the temperature is lowered, and difference in solubility by temperature is used to generate crystals, which are specific forms of solids. Therefore, seed crystals of L-α-glycerophosphorylcholine were required for crystal formation.

On the other hand, in the case of an embodiment according to the present invention, when an organic solvent was added to a liquid phase of L-α-glycerophosphorylcholine while maintaining temperature and stirring was performed, water was moved to the organic solvent and moisture in the L-α-glycerophosphorylcholine was reduced, and the property was transformed into a solid.

Figure 8:
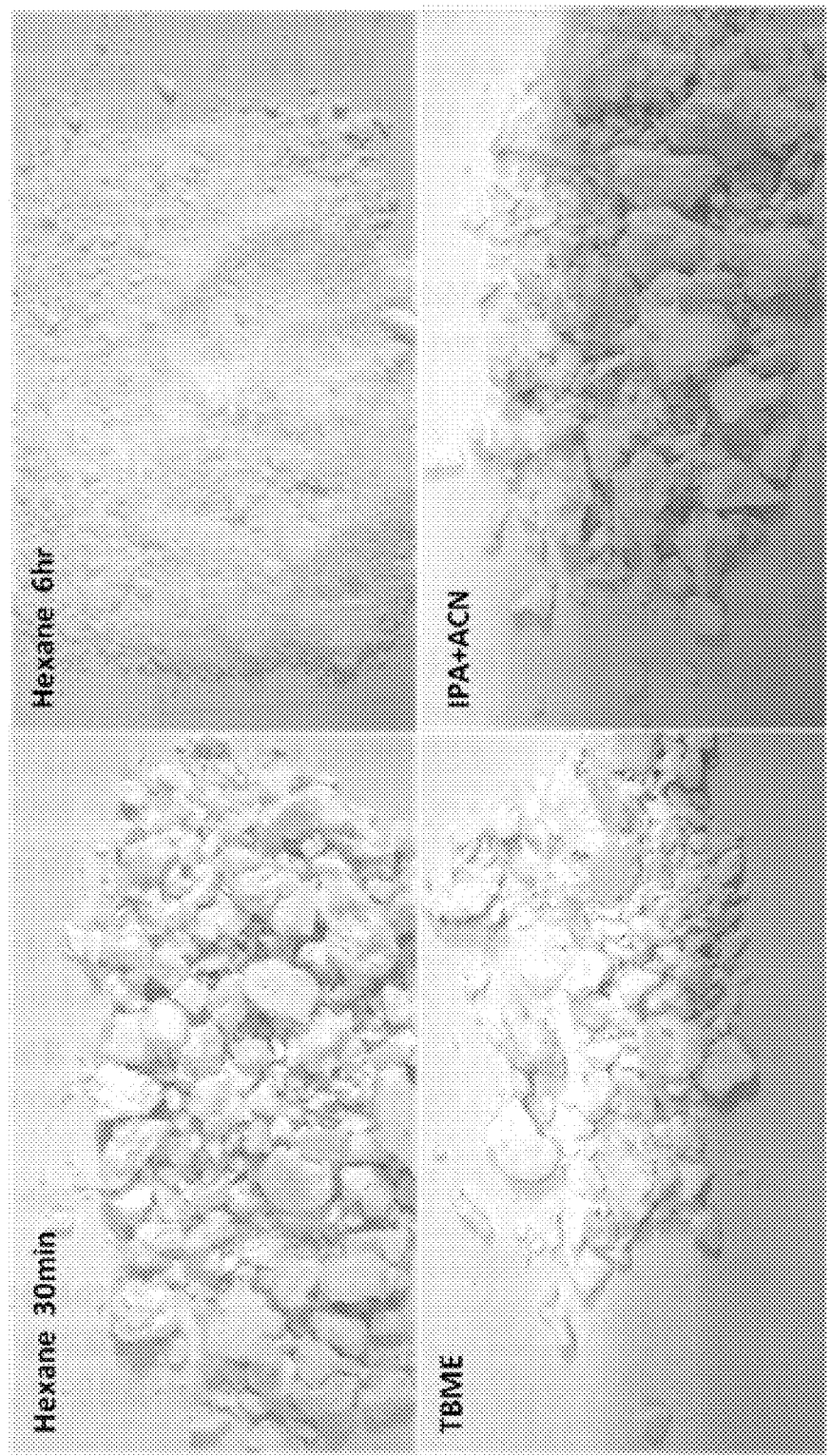
FIG. 8 shows images of the morphologies of a solid form of racemic or optically active D or L-α-glycerophosphorylcholine prepared according to an embodiment of the present invention.

It was also confirmed that powder X-ray diffraction (XRD), differential scanning calorimetry (DSC), and solid form were different depending on solvents, stirring time, temperature, and the like. FIGS. 1 to 4 showed differences in powder X-ray diffraction (XRD), FIGS. 5 to 7 showed differences in differential scanning calorimetry (DSC), and FIGS. 8 to 10 showed differences in properties of solid.

INDUSTRIAL APPLICABILITY

Compared to a conventional liquid form of racemic or optically active D or L-α-glycerophosphorylcholine, a solid form of racemic or optically active D or L-α-glycerophosphorylcholine prepared according to the present invention is easier to store and pack, is more stable, and has a higher purity. In addition, patient's medication compliance is high due to easy formulation modification and capacity change. Therefore, there is an advantage that various preparations can be mass-produced in a simple process.

Thus, specific portions of the present invention have been described in detail. It will be apparent to those skilled in the art that this specific description is only a preferred embodiment and that the scope of the present invention is not limited thereby. Accordingly, the actual scope of the present invention will be defined by the appended claims and equivalents thereof.

What is claimed is:

1. A method of preparing a solid form of racemic or optically active D or L-α-glycerophosphorylcholine, wherein a liquid phase of racemic or optically active D or L-α-glycerophosphorylcholine represented by Formula 1 below undergoes phase change by adding one or more organic solvents selected from the group consisting of alcohols, hydrocarbons, ketones, ethers and cyanides and stirring the mixture Formula 1

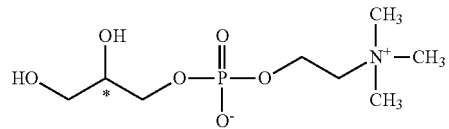

wherein * indicates a chiral center.

2. The method according to claim 1, wherein a liquid phase of racemic or optically active D or L-α-glycerophosphorylcholine is dried to a moisture content of 0 to 10% by weight, and then the organic solvents are added and stirred at a temperature of 0 to 70° C. for 0 to 24 hours.

3. The method according to claim 1, wherein the organic solvents are used in an amount of 1 to 20 times a volume of a liquid phase of racemic or optically active D or L-α-glycerophosphorylcholine.

4. The method according to claim 1, wherein the organic solvents are one or more selected from the group consisting of methanol, ethanol, n-propanol, isopropanol, n-butanol, isobutanol, 2-methoxyethanol, 2-ethoxyethanol, 2-butoxyethanol, 1-phentanol, 2-phentanol, 3-phentanol, 1-hexanol, 2-hexanol, 3-hexanol, 1-heptanol, 2-heptanol, 3-heptanol, 1-octanol, 2-octanol, 3-octanol, ethylene glycol, propylene glycol, dichloromethane, dichloroethane, n-pentane, n-hexane, cyclohexane, n-heptane, n-octane, toluene, xylene, naphtha, petroleum benzin, chloroform, carbon tetrachloride, trichloroethylene, perfluoropropane, acetone, methylethylketone, methylisobutylketone, acetophenone, propyl ether, n-butyl ether, tetrahydrofuran, diethyl ether, t-butyl methyl ether and acetonitrile.

5. The method according to claim 1, wherein the solid form of D or L-α-glycerophosphorylcholine exhibits peaks at 2θ diffraction angles of 11.9±0.2°, 14.2±0.2°, 19.8±0.2°, 25.3±0.2° and 40.4±0.2° in powder X-ray diffraction (XRD) analysis, and exhibits endothermic peaks in a range of 71±2° C. to 129±2° C. for endothermic onset temperature and endothermic peaks in a range of 100±2° C. to 137±2° C. for endothermic temperature in differential scanning calorimetry (DSC).

6. The method according to claim 1, wherein the solid form of D or L-α-glycerophosphorylcholine exhibits peaks at 2θ diffraction angles of 11.9±0.2°, 14.2±0.2°, 19.8±0.2°, 25.3±0.2° and 40.4±0.2° in powder X-ray diffraction (XRD) analysis, and exhibits an endothermic peak at 71±2° C. for endothermic onset temperature and at 100±2° C. for endothermic temperature, respectively, in differential scanning calorimetry (DSC).

7. The method according to claim 1, wherein the solid form of D or L-α-glycerophosphorylcholine exhibits peaks at 2θ diffraction angles of 9.7±0.2°, 11.9±0.2°, 14.2±0.2°, 19.8±0.2°, 25.3±0.2° and 40.4±0.2° in powder X-ray diffraction (XRD) analysis, and exhibits an endothermic peak at 129±2° C. for endothermic onset temperature and at 137±2° C. for endothermic temperature, respectively, in differential scanning calorimetry (DSC).

8. The method according to claim 1, wherein the solid form of D or L-α-glycerophosphorylcholine exhibits peaks at 2θ diffraction angles of 11.9±0.2°, 14.2±0.2°, 19.8±0.2°, 25.3±0.2°, 29.9±0.2° and 40.4±0.2° in powder X-ray diffraction (XRD) analysis, and exhibits an endothermic peak at 118±2° C. for endothermic onset temperature and at 132±2° C. for endothermic temperature, respectively, in differential scanning calorimetry (DSC).

9. The method according to claim 1, wherein the solid form of D or L-α-glycerophosphorylcholine exhibits peaks at 2θ diffraction angles of 11.9±0.2°, 14.2±0.2°, 15.7±0.2°, 19.8±0.2°, 25.3±0.2° and 40.4±0.2° in powder X-ray diffraction (XRD) analysis, and exhibits an endothermic peak at 105±2° C. for endothermic onset temperature and at 130±2° C. for endothermic temperature, respectively, in differential scanning calorimetry (DSC).

* * * * *